United States Patent [19]

Shaffer et al.

[11] Patent Number: 5,350,359
[45] Date of Patent: Sep. 27, 1994

[54] CONTROL, TREATMENT AND/OR DIAGNOSIS OF PHYSIOLOGICAL CONDITIONS WITH DEGASSED PERFLUOROCARBON LIQUID

[75] Inventors: Thomas H. Shaffer, Lansdowne; Marla R. Wolfson, Philadelphia, both of Pa.

[73] Assignee: Temple University of the Commonwealth System of Higher Education, Philadelphia, Pa.

[21] Appl. No.: 916,332

[22] Filed: Jul. 16, 1992

[51] Int. Cl.$^5$ ............................................. A61M 31/00
[52] U.S. Cl. ........................................ 604/51; 604/49; 128/898
[58] Field of Search ...................... 604/27, 28, 48, 49, 604/51, 50, 53; 128/898, 653.4, 654; 424/4, 9

[56] References Cited

U.S. PATENT DOCUMENTS

| | | |
|---|---|---|
| 2,503,650 | 4/1950 | Abramson . |
| 3,975,512 | 8/1976 | Long, Jr. . |
| 4,073,879 | 2/1978 | Long, Jr. . |
| 4,150,956 | 4/1979 | Basseen . |
| 4,183,962 | 1/1980 | Asher . |
| 4,232,665 | 11/1980 | Vaseen . |
| 4,285,928 | 8/1981 | Wada et al. . |
| 4,366,169 | 12/1982 | White . |
| 4,378,797 | 4/1983 | Osterholm . |
| 4,393,863 | 7/1983 | Osterholm . |
| 4,397,870 | 8/1983 | Sloviter . |
| 4,443,480 | 4/1984 | Clark, Jr. . |
| 4,445,500 | 5/1984 | Osterholm . |
| 4,445,514 | 5/1984 | Osterholm . |
| 4,445,886 | 5/1984 | Osterholm . |
| 4,445,887 | 5/1984 | Osterholm . |
| 4,445,888 | 5/1984 | Osterholm . |

(List continued on next page.)

FOREIGN PATENT DOCUMENTS

| | | |
|---|---|---|
| 4535797 | 11/1968 | Japan . |
| 59-130813 | 7/1984 | Japan . |
| 80/0068 | 1/1981 | PCT Int'l Appl. . |
| 89/04035 | 3/1991 | PCT Int'l Appl. . |

OTHER PUBLICATIONS

Sekins et al., "Intraccuitary and External Hypothermia of the Lung using PFC Liquids", Abstract: Ninth Annual Meeting of the North American Hyperthermia Group Presented in Seattle, Wash., Mar. 18–23 1989 p. 81–82.

Sekins, M. et al., "Lung Cancer Hyperthermia and PFC Liquids", Abstract: 5th International Symposium on (List continued on next page.)

*Primary Examiner*—C. Fred Rosenbaum
*Assistant Examiner*—V. Alexander
*Attorney, Agent, or Firm*—Seidel, Gonda, Lavorgna & Monaco

[57] ABSTRACT

This invention pertains to the use of a degassed perfluorocarbon ("PFC") liquid as a method of removing gas emboli from parts of a patient's internal anatomy. Moreover, the invention can be used as a method of imaging parts of a patient's internal anatomy. Furthermore, the invention can also be used as a way of delivering biological agents to parts of a patient's internal anatomy which contain or are surrounded by gas emboli and/or which are to be imaged. In this invention, a degassed PFC liquid is delivered to a region within the patient's internal anatomy which contains gas emboli and/or which is to be imaged. If gas emboli are present, the degassed liquid is permitted to absorb at least a portion of the emboli. Thereafter, the emboli-containing liquid is removed from the patient or is used as an imaging agent. If gas emboli are not present, the cite is imaged before the degassed liquid reaches atmospheric equilibrium. Thereafter, the liquid is removed from the patient. Moreover, by mixing a biological agent with the degassed PFC liquid, the mixture can be used as a way of topically treating parts within a patient's internal anatomy. Furthermore, by regulating the temperature of the degassed liquid, it can also be used as a way of hypo- or hyperthermically treating the patient.

12 Claims, 9 Drawing Sheets

U.S. PATENT DOCUMENTS

| | | |
|---|---|---|
| 4,446,154 | 5/1984 | Osterholm . |
| 4,446,155 | 5/1984 | Osterholm . |
| 4,450,841 | 5/1984 | Osterholm . |
| 4,451,251 | 5/1984 | Osterholm . |
| 4,452,818 | 6/1984 | Haidt . |
| 4,461,717 | 7/1984 | Moore . |
| 4,490,351 | 12/1984 | Clark, Jr. . |
| 4,568,327 | 2/1986 | Seufert ................................. 604/5 |
| 4,640,833 | 2/1987 | Tambroski et al. . |
| 4,657,532 | 4/1987 | Osterholm . |
| 4,686,085 | 8/1987 | Osterholm . |
| 4,758,431 | 7/1988 | Osterholm . |
| 4,767,610 | 8/1988 | Long . |
| 4,769,241 | 9/1988 | Heldebrant et al. . |
| 4,781,676 | 11/1988 | Schweighardt et al. . |
| 4,795,423 | 1/1989 | Osterholm . |
| 4,830,849 | 5/1989 | Osterholm . |
| 4,833,274 | 5/1989 | Caporiccio et al. . |
| 4,865,836 | 9/1989 | Long, Jr. . |
| 4,879,062 | 11/1989 | Moore . |
| 4,895,719 | 1/1990 | Radahkrishnan et al. . |
| 4,917,930 | 4/1990 | McCormick . |
| 4,927,623 | 5/1990 | Long, Jr. . |
| 4,951,673 | 8/1990 | Long . |
| 4,963,130 | 10/1990 | Osterholm . |
| 4,963,367 | 10/1990 | Ecanow . |
| 4,981,691 | 1/1991 | Osterholm et al. . |
| 4,985,550 | 1/1991 | Charpiot et al. . |
| 4,987,154 | 1/1991 | Long, Jr. . |
| 5,158,536 | 10/1992 | Sekins et al. .................... 604/20 |

OTHER PUBLICATIONS

Hyperthermic Ocology, Kyoto, Japan. – Aug. 29–Sep. 5 1988 p. 159, pp. 78–80.

Spiess, B. D., et al. "Protection from Coronary Air Embolism by a Perfluorocarbon Emulsion", *Journal of Cardiothoracic Anethesia*, vol. 1, No. 3 (Jun), 1987 pp. 210–215.

Spiess, B. D. et al., "Protection from Venous Air Embolism with Fluorocarbon Emulsion FC–43", *Journal of Surgical Research* 41(4), pp. 439–444, (1986).

Strickling, H. L., "Liquid Composition for Rinsing the Respiratory Systems of Mammals", *Pharmaceuticals*, vol. 79, 35133d, p. 219 (1973).

Boren, H. G., "Deposition and Removal of Carbon Particles by Fluorocarbon Breathing", *Federation Proceedings*, vol. 29, No. 5, pp. 1737–1739 (Sep–Oct 1970).

Modell, J. H., et al., "Long–Term Survival of Dogs After Breathing Oxygenated Fluorocarbon Liquid", *Federation Proceedings*, vol. 29, No. 5, pp. 1731–1736 (Sep–Oct 1970).

FIG. IA
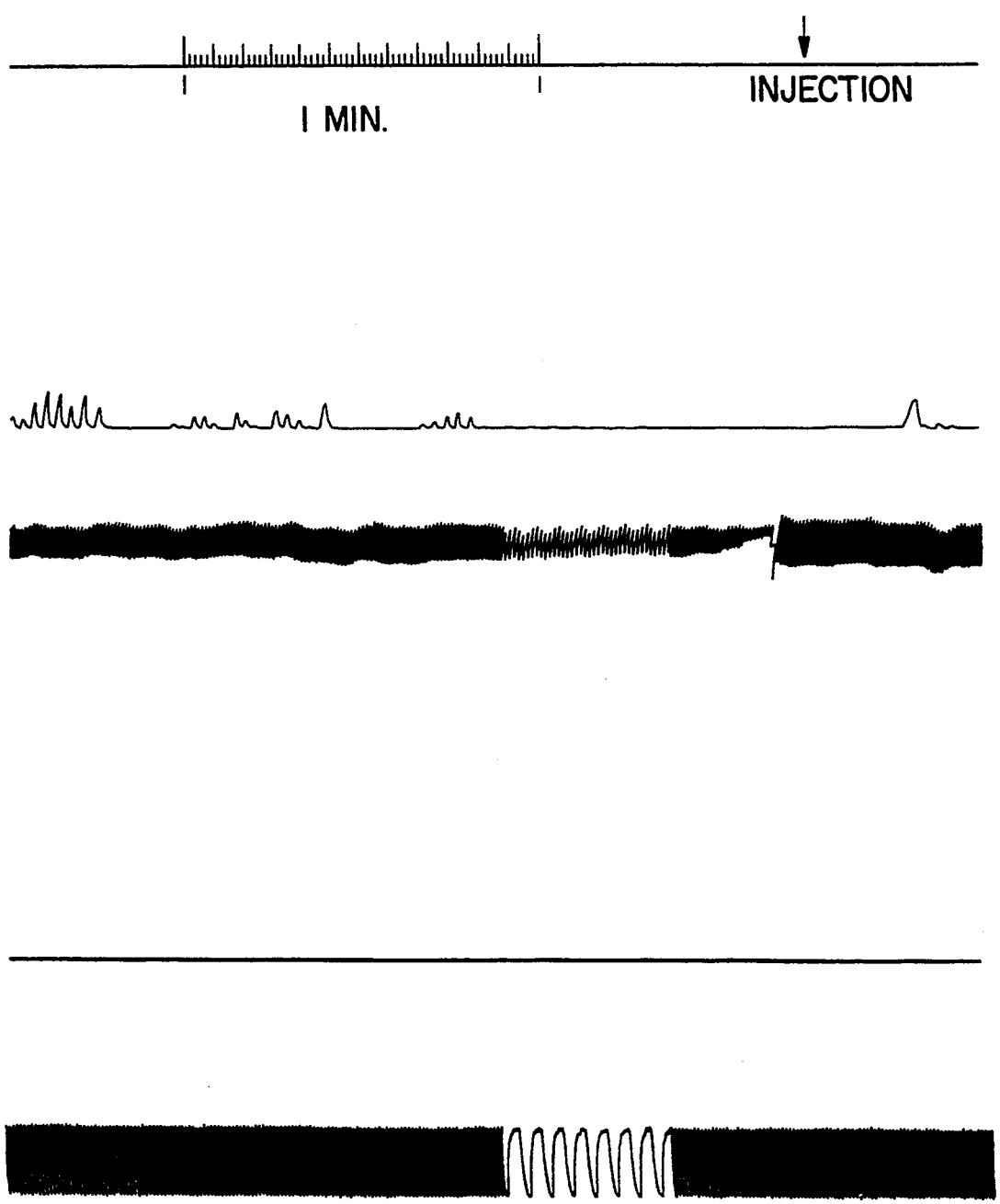

1 MIN.

CONTROL, TREATMENT AND/OR DIAGNOSIS OF PHYSIOLOGICAL CONDITIONS WITH DEGASSED PERFLUOROCARBON LIQUID

FIELD OF THE INVENTION

The invention relates to the use of degassed perfluorocarbon liquid ingestion and/or infusion as a means for controlling, treating and/or diagnosing physiological conditions within a patient. In particular, degassed perfluorocarbon liquid can be used as a means for imaging parts of a patient's body cava, as a means for delivering biological agents to parts of a patient's body cava, and/or as a means for absorbing gas(es) from parts of a patient's body cava.

BACKGROUND OF THE INVENTION

It is known to use "gassed" (e.g., oxygenated) perfluorocarbon liquids as a means for delivering gases (e.g., oxygen) to certain parts of a patient's pulmonary and/or vascular systems. Moreover, it is also known to use atmospheric-equilibrated perfluorocarbon liquids as a contrast mediums for imaging purposes.

This invention pertains to novel applications of "degassed" perfluorocarbon liquids. Specifically, the present invention pertains to using degassed perfluorocarbon liquids as a means for controlling, treating and/or diagnosing certain physiological conditions, diseases and/or abnormalities of a patient which were, heretofore, difficult or impossible to control, treat and/or diagnose.

DEFINITIONS

As used herein, the term "gassed perfluorocarbon liquid" refers to a perfluorocarbon liquid which has been forced to absorb gas(es) such that the total concentration of gas contained therein is greater than that present in the same liquid at atmospheric equilibrium conditions.

As used herein, the term "oxygenated perfluorocarbon liquid" refers to a specific type of gassed perfluorocarbon liquid which has been forced to absorb oxygen such that the total concentration of oxygen contained therein is greater than that present in the same liquid at atmospheric equilibrium conditions.

As used herein, the term "degassed perfluorocarbon liquid" refers to a perfluorocarbon liquid which has been forced to release gas(es) such that the total concentration of gas contained therein is less than that present in the same liquid at atmospheric equilibrium conditions.

As used herein, the term "atmospheric-equilibrated perfluorocarbon liquid" refers to a perfluorocarbon liquid having a concentration of gas contained therein which is substantially the same as that present in the same liquid prior to being gassed or degassed.

As used herein, the term "body cava" refers to cavities, spaces, voids and/or gaps present in and/or around regions, parts, and/or organs within a patient's internal anatomy. Various locations within a patient's internal anatomy encompassed by the term "body cava", include, without limitation, cavities, spaces, voids and/or gaps present in and/or around the patient's gastrointestinal track, uterus, bladder, nasal cavity, sinus cavity and acoustic canal.

SUMMARY OF THE INVENTION

One object of this invention is to provide a novel means for removing gas emboli from a patient's body cava.

Another object of this invention is to provide a novel means for imaging portions of a patient's body cava.

Yet another object of this invention is to provide a novel means for imaging portions of a patient's body cava which contain and/or are at least partially surrounded by gas emboli.

Even another object of this invention is to provide a novel means for delivering biological agents to locations within a patient's body cava which are to be imaged.

A further object of this invention is to provide a novel means for delivering biological agents to locations within a patient's body cava which contain and/or are at least partially surrounded by gas emboli.

Even a further object of the present invention is to provide a novel means for delivering biological agents to locations within a patient's body cava which contain and/or are at least partially surrounded by gas emboli and which are to be imaged.

One embodiment of this invention pertains to the use of a degassed perfluorocarbon ("PFC") liquid as a novel means for removing gas emboli from a patient's body cava. In this embodiment, gas emboli within a patient's body cava are removed by a process which comprises the following steps: (a) degassing a PFC liquid, (b) delivering the degassed PFC liquid to a region within the patient's body cava containing a gas emboli, (c) permitting the degassed PFC liquid to absorb at least a portion of the gas emboli, and (d) removing from the patient's body cava the emboli-containing PFC liquid.

Another embodiment of this invention pertains to the use of a degassed PFC liquid as a novel means for imaging parts of a patient's internal anatomy. In this embodiment, parts of a patient's internal anatomy can be imaged by a process which comprises the following steps: (a) degassing a PFC liquid, (b) delivering the degassed PFC liquid to a region within the patient's body cava which is to be imaged, (c) imaging the region within the patient's internal anatomy to which the degassed PFC liquid was delivered, and (d) removing from the patient's body cava the PFC liquid.

Yet another embodiment of this invention pertains to the use of a degassed PFC liquid as a novel means for imaging parts of a patient's internal anatomy which contain and/or are at least partially surrounded by gas emboli. In this embodiment, such parts of a patient's internal anatomy can be imaged by a process which comprises the following steps: (a) degassing a PFC liquid, (b) delivering the degassed PFC liquid to a region within the patient's body cava which is to be imaged and which contains and/or is at least partially surrounded by a gas emboli, (c) permitting the degassed PFC liquid to absorb at least a portion of the gas emboli, (d) imaging the region within the patient's internal anatomy which contained or was surrounded by the gas emboli, and (e) removing from the patient's body cava the emboli-containing PFC liquid.

Even another embodiment of this invention pertains to the use of a degassed PFC liquid as a novel means for delivering biological agents to parts of a patient's internal anatomy which are to be imaged. In this embodiment, biological agents can be provided to such parts of a patient's internal anatomy by a process which comprises the following steps: (a) degassing a PFC liquid, (b) mixing a biological agent with the degassed PFC liquid to form an agent-containing PFC liquid, (c) delivering the agent-containing PFC liquid to a region within the patient's body cava which is to be imaged, (d) permitting at least some of the biological agent to be released from the agent-containing PFC liquid, (e) imaging the region within the patient's internal anatomy to which the agent-containing PFC liquid was delivered, and (f) removing from the patient's body cava the PFC liquid.

A further embodiment of this invention pertains to the use of a degassed PFC liquid as a novel means for delivering biological agents to parts of a patient's internal anatomy which contain and/or are at least partially surrounded by gas emboli. In this embodiment, biological agents can be provided to such parts of a patient's internal anatomy by a process which comprises the following steps: (a) degassing a PFC liquid, (b) mixing a biological agent with the degassed PFC liquid to form an agent-containing PFC liquid, (c) delivering the agent-containing PFC liquid to a region within the patient's body cava which contains and/or is at least partially surrounded by a gas emboli, (d) permitting the agent-containing PFC liquid to absorb at least a portion of the gas emboli, (e) permitting at least some of the biological agent to be released from the agent-containing PFC liquid, and (f) removing from the patient's body cava the emboli-containing PFC liquid.

Even a further embodiment of this invention pertains to the use of a degassed PFC liquid as a novel means for delivering biological agents to parts of a patient's internal anatomy which are to be imaged and which contain and/or are at least partially surrounded by gas emboli. In this embodiment, biological agents can be provided to such parts of a patient's internal anatomy by a process which comprises the following steps: (a) degassing a PFC liquid, (b) mixing a biological agent with the degassed PFC liquid to form an agent-containing PFC liquid, (c) delivering the agent-containing PFC liquid to a region within the patient's body cava which is to be imaged and which contains and/or is at least partially surrounded by a gas emboli, (d) permitting the agent-containing PFC liquid to absorb at least a portion of the gas emboli, (e) permitting at least some of the biological agent to be released from the agent-containing PFC liquid, (f) imaging the region within the patient's internal anatomy to which the PFC liquid was delivered, and (g) removing from the patient's body cava the emboli-containing PFC liquid.

These and other objects, embodiments and aspects of the present invention will become apparent to those skilled in the art upon reading the following detailed description.

BRIEF DESCRIPTION OF THE DRAWINGS

A more complete appreciation of the invention will be readily obtained as the same becomes better understood by reference to the following detailed description and the accompanying figures briefly described below.

FIGS. 1A-B are a print-out from a pressure transducer showing the changes in bowel motility resulting from infusing a neat, degassed PFC liquid into the bowel of a neonatal lamb.

DETAILED DESCRIPTION OF THE INVENTION

Figure 1B:
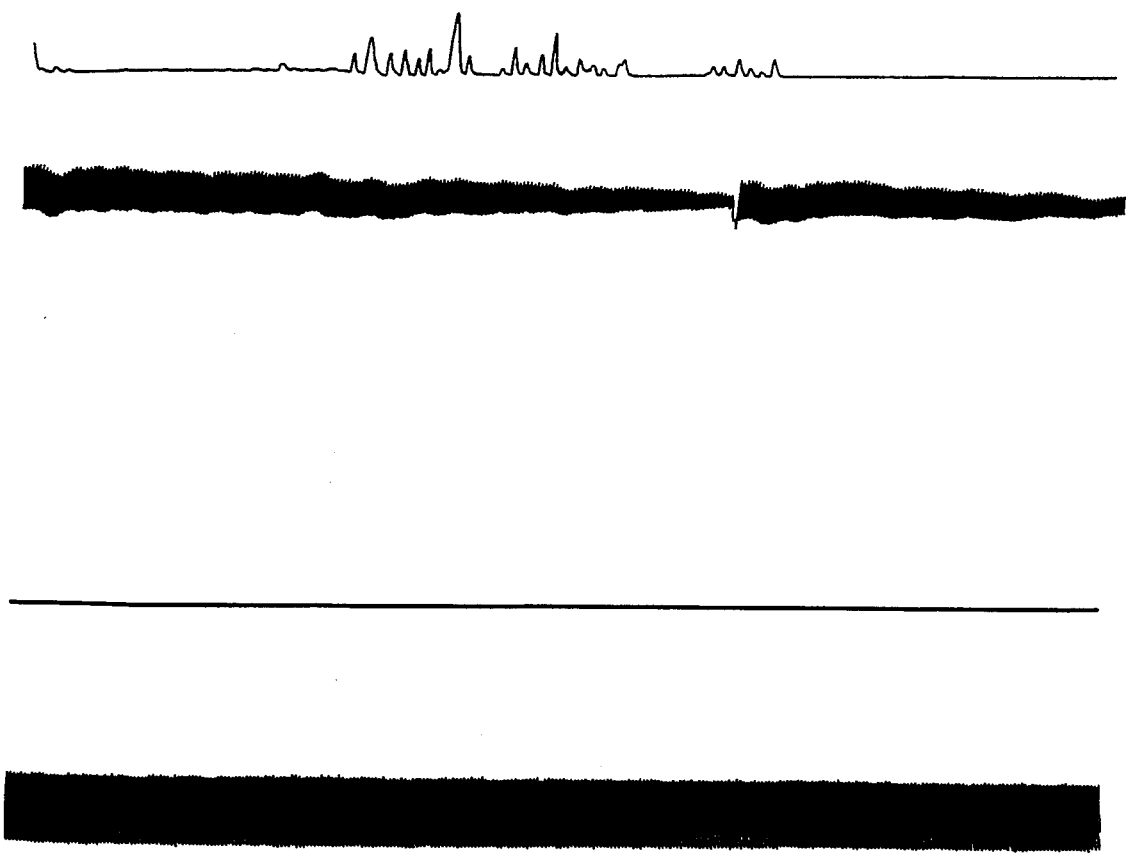

The presence of gas emboli which are in and/or around certain parts of a patient's body cava have been the source of many different types of problems to the patient and the medical practitioner. For example, their presence can subject a patient to severe health hazards. Specifically, their presence may have adverse effects on the internal body parts which they are in and/or around. Moreover, their presence may hinder the imaging of certain internal body parts; thus, rendering this highly useful diagnostic tool ineffective. Furthermore, their presence may also hinder the treatment of certain internal body parts with the appropriate biological agents. This invention provides a novel process which resolves each of the above problems.

In addition to the above, this invention also provides a novel process for performing the following procedures: imaging regions within a patient's internal anatomy; and, delivering biological agents to parts of a patient's body cava which are to be imaged.

For those instances where the presence of gas emboli have an adverse effect on a patient's physiological condition, one embodiment of this invention provides a novel means for their removal through the use of a degassed PFC liquid. Here, a suitable PFC liquid is at least partially degassed. The level to which the PFC liquid is degassed depends, in part, upon the size and location of the gas emboli.

PFC liquids can be degassed by any means known to those skilled in the art. In one of the more preferred degassing methods, a vacuum source is attached to a sealed reservoir containing an atmospheric-equilibrated PFC liquid. Generally, this vacuum source is at least about $-30$ mm Hg.

The driving force created by the vacuum vaporizes the PFC liquid. The vaporized PFC liquid is condensed by being drawn through a cold condenser unit. The condensed PFC vapor has a gas concentration less than that within the atmospheric-equilibrated PFC liquid. In order to prevent reabsorption, gases which were evacuated during the condensation process are appropriately vented.

After the PFC liquid has been degassed to the desired level, it is delivered to that region within the patient's body cava which contains the gas emboli to be removed. Any suitable means can be used to deliver the degassed PFC liquid to the appropriate region. Examples of suitable delivery techniques include, without limitation, ingestion, injection, inhalation and infusion. The preferred delivery technique depends, in part, upon the location of the emboli.

When the degassed PFC liquid comes into contact with the gas emboli, the liquid will begin to absorb the gas. Generally, the PFC liquid is permitted to remain at that location until the emboli is completely absorbed by the PFC liquid or until the degassed PFC liquid has reached equilibrium. However, it is within the scope of this invention to terminate the absorption process before the emboli is completely absorbed and before the degassed PFC liquid has reached equilibrium if so desired.

After the PFC liquid has absorbed the desired amount of the gas emboli, the now emboli-containing PFC liquid is removed from the patient's body cava. This PFC liquid can be removed by any suitable means. For example, the emboli-containing PFC liquid can be physically withdrawn and/or drained via appropriate medical devices (e.g., a syringe, a catheter, etc.), or withdrawn via natural means (e.g., through normal body excretions). If the gas emboli was not completely removed, the aforementioned process can be repeated if so desired.

Heretofore, the medical profession was not aware of such a process for the removal of gas emboli. Accordingly, this embodiment of the invention, opens many new avenues for treating patients which have been plagued by the presence of gas emboli.

Another problem resolved by this invention pertains to those instances where the presence of gas emboli hinders the clear imaging of certain regions of a patient's internal anatomy. Specifically, a highly useful diagnostic tool in the medical profession is the imaging of certain body parts by non-invasive procedures such as ultrasonic imaging and MRI imaging. If gas emboli are present in and/or around the particular region being imaged, their presence can decrease the clarity of the image. Depending upon the amount of gas emboli present and the imaging technique being employed, their presence can render the resulting image completely unusable.

In this embodiment, a degassed PFC liquid is delivered to the region within the patient's body cava which is to be imaged and which contains and/or is at least partially surrounded by gas emboli. As stated above, any suitable means can be used for degassing the PFC liquid.

The degassed PFC liquid is permitted to stay in contact with the emboli until the gas is completely absorbed thereby or until equilibrium conditions are reached. If equilibrium is reached before the gas emboli is completely removed from the imaging cite, it is presently preferred to repeat this process since the presence of gas emboli often decreases the clarity of most images.

After a sufficient amount of the gas emboli has been removed from or around the cite which is to be imaged, the imaging process is commenced. Due to the excellent imaging properties of PFC liquids, it is presently preferred to keep the liquid at the imaging cite during the imaging process.

When the PFC liquid absorbs the gas emboli, the resultant composition is not a two phase mixture. Rather, the emboli is dissolved into the PFC liquid to form a homogenous solution. Although applicants have discovered that the imaging properties of a degassed PFC liquid are better than those of a similar atmosphere-equilibrated PFC liquid (the specifics of this discovery will be discussed later), in many instances, the imaging properties of an atmospheric-equilibrated PFC liquid are satisfactory. Therefore, unless exceptional clarity is desired, the emboli-containing PFC liquid can be retained at the imaging cite throughout the imaging process.

Notwithstanding the above, it is also within the purview of this invention to replace the emboli-containing PFC liquid with a degassed liquid prior to commencing the imaging process. As stated above, this feature of the invention will be discussed later. Moreover, if desired, all PFC liquids can be removed before imaging is begun.

Even if there is no PFC liquid present at the imaging cite, the advantages of this invention can still be appreciated. For example, the degassed PFC liquid would have removed at least a part of a gas emboli which would have distorted the image. Also, if the PFC liquid is removed, it will probably carry with it some loose particles from the cite which would also have distorted the image.

While any suitable imaging devise can be used, there are some which benefit more from this invention. For example, ultrasonic imaging techniques work on the concept of reflected sound waves. Since the presence of gas emboli affects the way in which sound waves are reflected, the features of this invention are greatly appreciated by those who implement this imaging process.

On the other hand, as the name suggests, MRI imaging techniques work on the concept of magnetic resonance. Gas emboli effect sound waves more than they effect magnetic fields. Therefore, while it is still advantageous to employ the process of this invention when implementing an MRI imaging technique, sound wave-based imaging techniques benefit more from its use.

If the PFC liquid is retained at the imaging cite during the imaging process, after the process is completed, it is removed from the patient's body cava. As stated above, the PFC liquid can be removed by any suitable means (e.g., physically, naturally, etc.).

As can be seen from the above, by practicing this embodiment of the invention, medical practitioners can now use diagnostic tools which were heretofore ineffective on patients plagued by the presence of gas emboli in and/or around the imaging cite (e.g., ultrasonic techniques). Moreover, for those imaging techniques which are not as adversely effected by the presence of gas emboli (e.g., MRI techniques), practicing this embodiment of the invention can improve their clarity and/or effectiveness.

Yet another problem solved by this invention pertains to those instances where it is desirable to deliver biological agents to parts of a patient's body cava which contain and/or are at least partially surrounded by gas emboli. For example, in many instances it is desirable to topically apply biological agents to certain parts of a patient's internal anatomy. Under conventional practices, the presence of gas emboli may create a barrier prohibiting this type of treatment and/or may produce undesired complications.

In this embodiment of the invention, a mixture of a biological agent and a degassed PFC liquid is delivered to the cite where the biological agent is to have its desired effect and which contains and/or is at least partially surrounded by gas emboli. As stated earlier, any suitable means can be used for degassing the PFC liquid and for delivering the liquid to its desired cite.

When practicing this embodiment of the invention, the biological agent can be mixed with the PFC liquid either before, during or after the degassing procedure. For obvious reasons, if the biological agent is normally in a gaseous phase, it is preferred to mix this agent with the PFC liquid after the degassing process is completed.

On the other hand, if the agent is normally in a solid or liquid phase, in most instances it can be mixed with the PFC liquid at any time prior to introducing the mixture into the patient. However, in order not to create any complications during the degassing process, it is generally preferred to also mix these types of biological agents with the PFC liquid after it has been degassed.

Any suitable means can be used for introducing the biological agent into the PFC liquid. For example, the agent can be introduced in a time released manner or in a bulk form. The preferred method of introduction will depend, in part, upon the specific agent being introduced, upon the desired effect of the specific agent, and/or upon the patient's specific physiological conditions.

As used herein, the term "biological agent" refers to any agent which can be carried by and/or dissolved into the PFC liquid. Examples of suitable types of biological agents include, without limitation, medicaments, muscle relaxing agents, muscle contraction agents and image enhancing agents.

As before, once the agent-containing degassed PFC liquid comes into contact with the gas emboli, the absorption process will begin. The PFC liquid is permitted to remain at this cite until the emboli is completely absorbed or until equilibrium conditions are reached.

However, prior to removing the PFC liquid from the patient's body cava, at least some of the biological agent is permitted to be released therefrom to the surrounding area. Therefore, in this embodiment, the PFC liquid should be removed from the patient's body cava only after it has (a) absorbed the desired amount of the gas emboli therein, and (b) released the desired amount of the biological agent therefrom. After the above has been completed, the PFC liquid can be removed from the patient's body cava by any suitable means.

Each of the embodiments of this invention can be practiced independently from, or in combination with one another. For example, by practicing this invention, a medical professional can now (a) remove gas emboli from a patient's body cava, (b) image a cite within a patient's internal anatomy which contains or is surrounded by gas emboli, (c) deliver biological agents to a cite within a patient's internal anatomy which contains or is surrounded by gas emboli, and/or (d) deliver biological agents to a cite within a patient's internal anatomy which not only contains or is surrounded by gas emboli; but also, is to be imaged. One of the novel features of this invention is that all of the above can now be performed by a single process.

This invention can also be employed as a means for controlling, treating and/or diagnosing physiological conditions within a patient which is not troubled by the presence of gas emboli. Specifically, a further embodiment of this invention pertains to a novel means for imaging regions within a patient's internal anatomy.

In this embodiment, a degassed PFC liquid is delivered to or around the cite which is to be imaged. Then, prior to the degassed PFC liquid reaching atmospheric equilibrium through the absorption of miscellaneous body gases, the region to which the degassed PFC liquid was delivered is imaged. Thereafter, the degassed PFC liquid is removed from the patient's body.

In even a further embodiment of this invention, a degassed PFC liquid is mixed with a biological agent. Thereafter, the mixture is delivered to a region within the patient's body cava which is to be treated and/or affected by the biological agent and which is to be imaged. While the agent-containing liquid is at the appropriate cite, and before the agent-containing liquid has reached atmospheric equilibrium, that region of the patient's internal anatomy can be imaged. After the imaging process is completed and after the biological agent has had its desired effect, the PFC liquid is removed from the patient's body cava.

It is also within the purview of this invention to use the degassed PFC liquid as a means for heating and/or cooling specific body cavities. Specifically, prior to introducing the degassed PFC liquid into the patient, its temperature is adjusted accordingly. Therefore, in addition to the aforementioned features of this invention, it can also be designed to hypo- or hyperthermically treat the patient.

The following examples are presented for illustrative purposes only. They are not to be construed as limiting the invention to the specific conditions involved therein.

EXAMPLE I

The following data demonstrates the functional changes in bowel motility by practicing the present invention. This data was obtained in a male neonatal lamb. The subject was 5 days postnatal age and weighed approximately 4.8 kilograms.

Prior to performing any surgical procedure on the subject, it was anesthetized with pentobarbital sodium. This was accomplished by an intraperitoneal bolus of 25 mg/kg followed by maintenance intravenous administration of 3 mg/kg/hr.

The anesthetized subject was then gas ventilated and managed according to standard protocols to maintain physiologic gas exchange and acid-base conditions.

Thereafter, the animal was instrumented as follows to assess functional changes in bowel motility. First, under local anesthesia, a small incision was made in the subject's abdominal wall. The duodenum-pylorus junction was palpated and the duodenum was incised 2 cm below this junction.

A gas-filled balloon tipped catheter was then inserted. Its tip was positioned 10 cm caudal to the incision. Thereafter, a saline-filled catheter was inserted through the same incision. Its tip was positioned 20 cm caudal to the incision. Once both catheters were secured by purse string sutures, the subject's abdominal wall was clipped and closed.

The gas-filled balloon tipped catheter was connected to a Statham P23BC pressure transducer to measure pressure changes in response to agents which were manually infused through the saline-filled catheter. Pressure changes were used as an index of alterations in bowel motility pattern, following the infusion of: (a) a 5 ml bolus of neat PFC; (b) a 5 ml bolus of combined PFC and acetone (ACh:1.0 mg/kg); and (c) a 5 ml bolus of combined PFC and epinephrine (EPI:0.50 mg/kg).

Following the infusion of a 5 ml bolus of neat PFC liquid through the saline-filled catheter, there was a small but unsustained increase in motility. The monitored results from the pressure transducer are reproduced in FIG. 1. Such a finding is common to any volume of fluid ostensibly associated with the stimulation of mechanoreceptors and myogenic responses.

Figure 2:
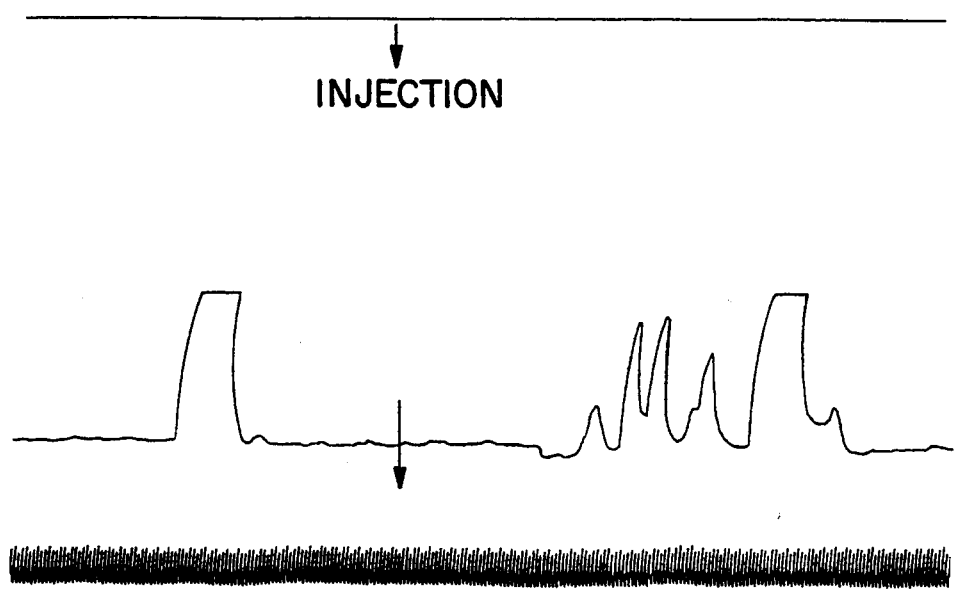
FIG. 2 is a print-out from a pressure transducer showing the changes in bowel motility resulting from infusing a mixture of a degassed PFC liquid and epinephrine into the bowel of a neonatal lamb.
Figure 2:
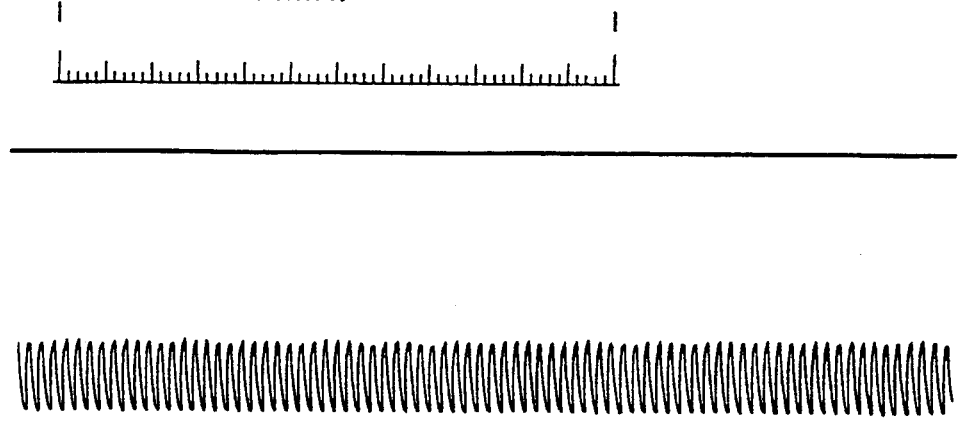
Figure 3A:
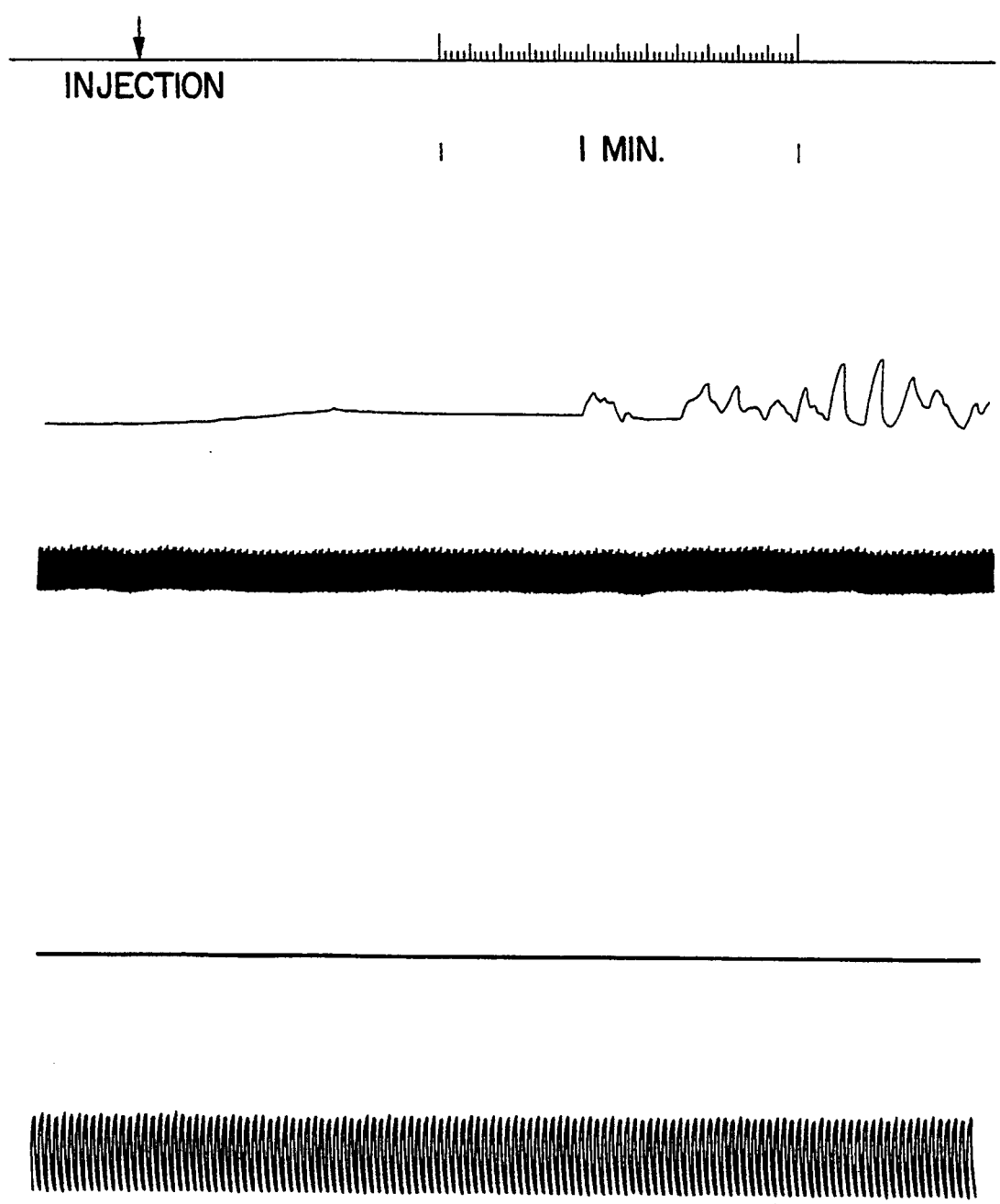
FIGS. 3A-E are a print-out from a pressure transducer showing the changes in bowel motility resulting from infusing a mixture of a PFC liquid and acetylcholine into the bowel of a neonatal lamb.
Figure 3B:
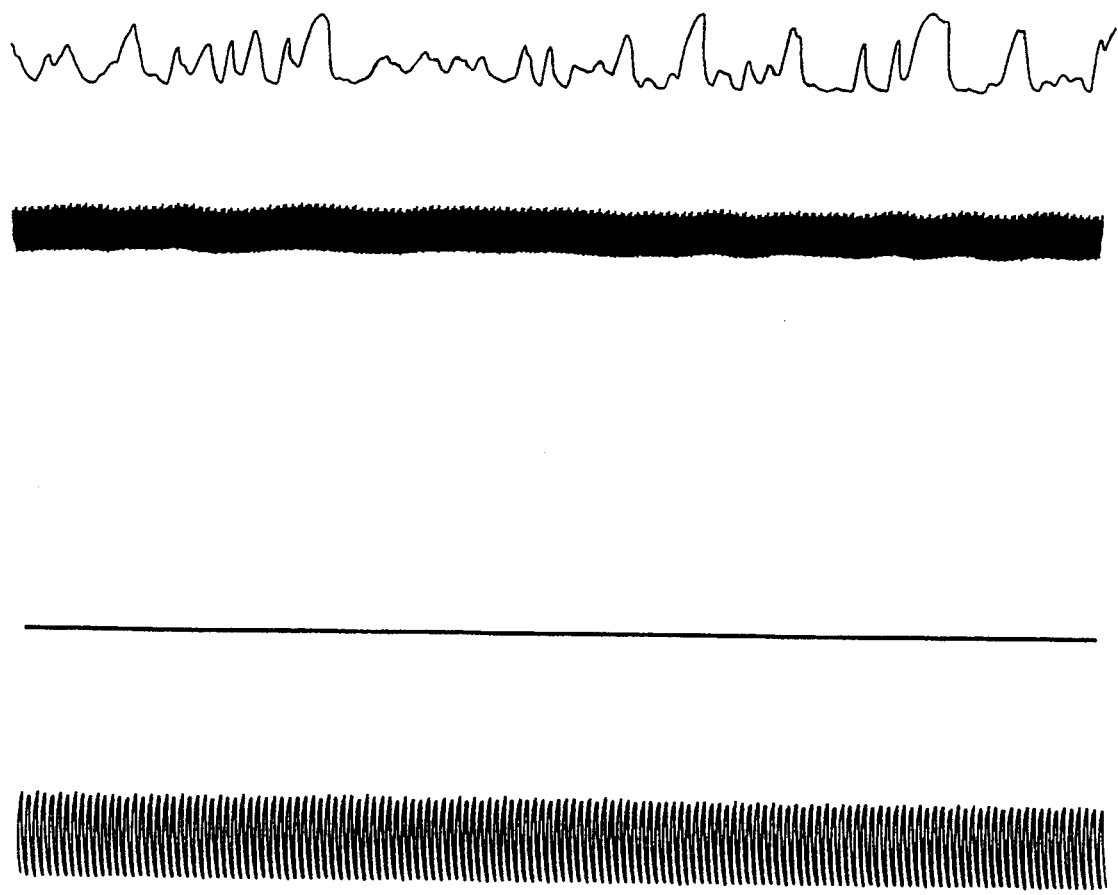
Figure 3C:
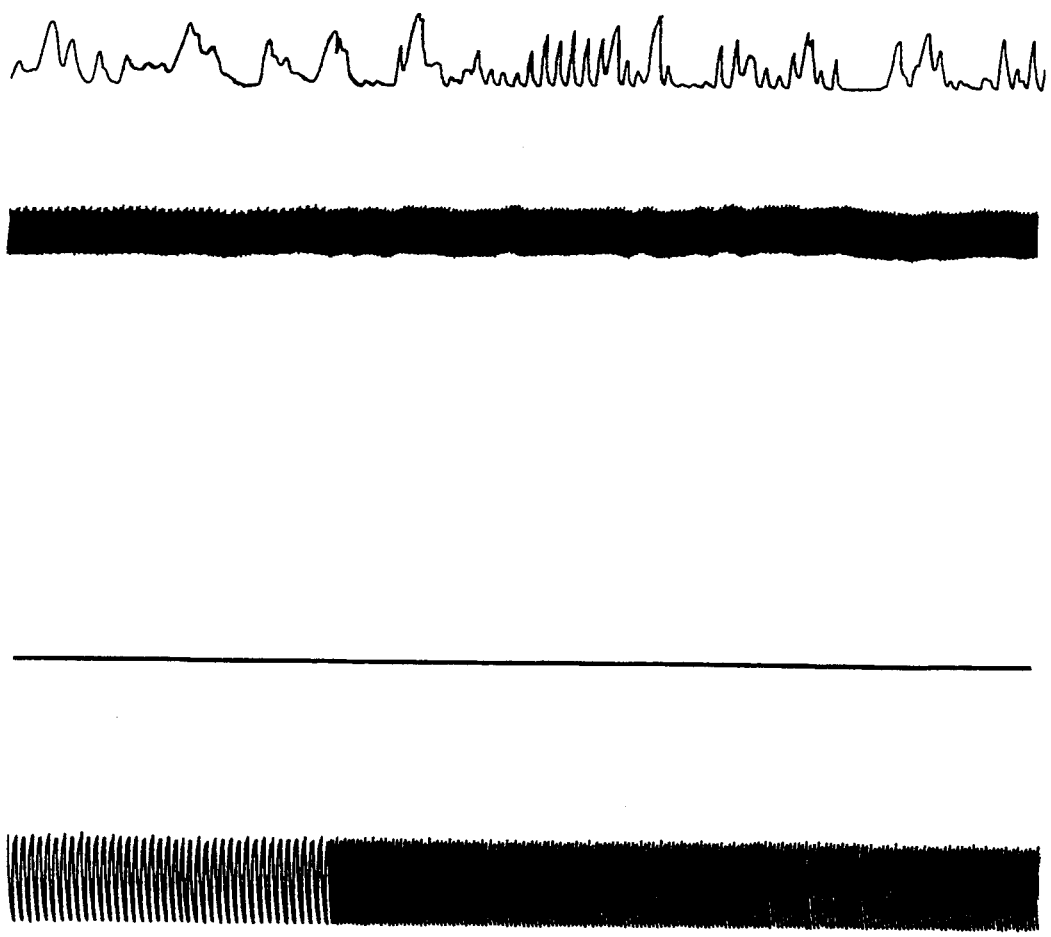
Figure 3D:
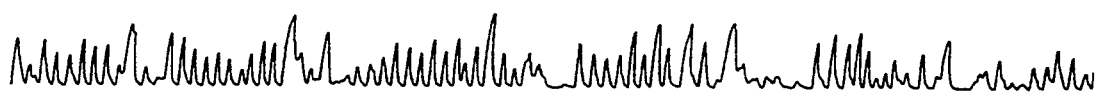
Figure 3D:
Figure 3D:
Figure 3E:
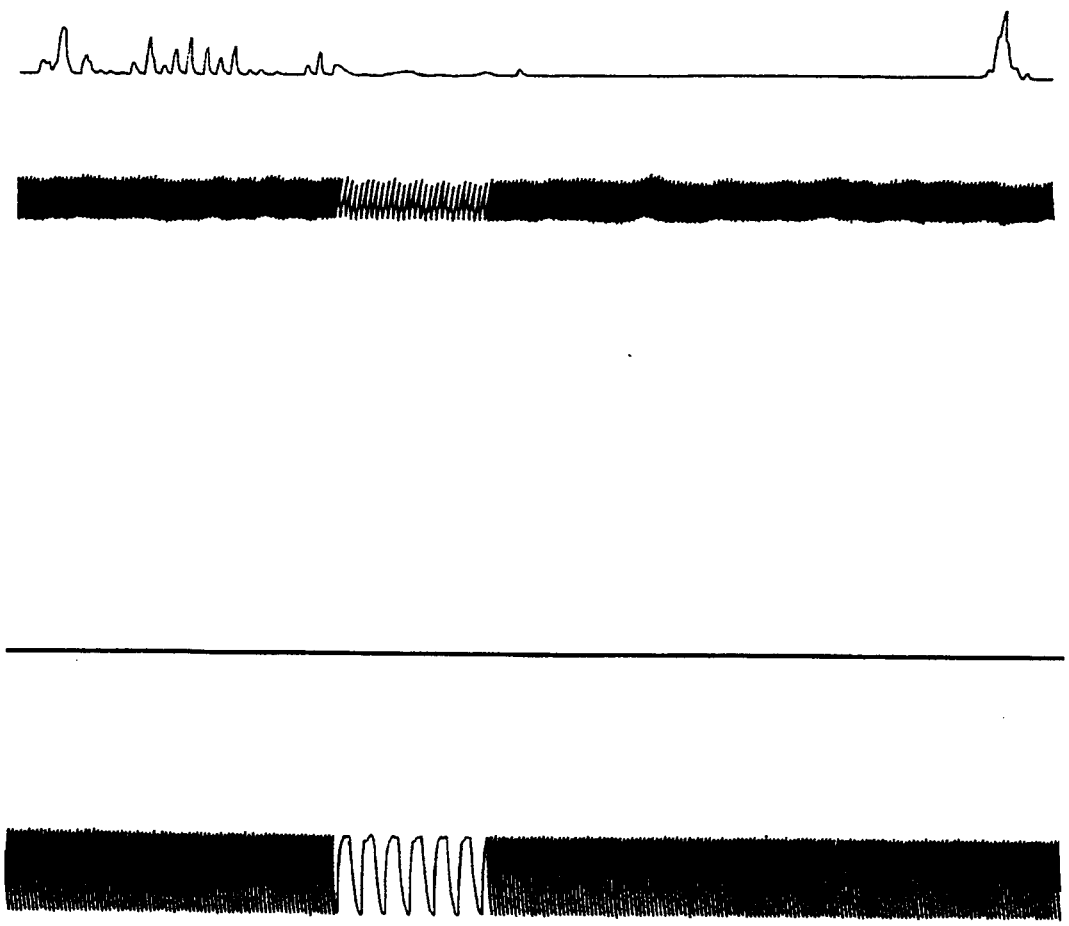

Following the infusion of a 5 ml bolus of a PFC/epinephrine mixture (EPI: 0.5 mg/kg) through a saline-filled catheter, the change in the motility pattern was relatively small. The monitored results from the pressure transducer are reproduced in FIG. 2. Such a response is generally associated with sympathomimetic relaxation of smooth muscle in the intestine.

Following the infusion of a 5 ml bolus of a PFC/acetone mixture (ACh:1.0 mg/kg) through the saline-filled catheter, the bowel motility and tone was increased. The monitored results from the pressure transducer are reproduced in FIG. 3. This generally increases smooth muscle contraction in the bowel.

Although not preferred, the bowel could have been continuously imaged to synchronize functional pressure activity with dimensional alterations throughout the three conditions. If performed, functional changes could have been assessed relative to the mode of administering the agent (i.e., bolus vs. infusion of equivalent doses of the agent).

EXAMPLE II

In this example, in vitro and in vivo testing of saturated and unsaturated PFC liquids was performed.

Regarding in vitro testing, studies were preformed on the acoustic characteristics of PFC liquids. These studies demonstrated that the presence of cavitation (i.e., the creation of gas bubbles freed from solution) is related to the amount of gas dissolved in the PFC liquid. The results of these studies are reproduced in the graphs illustrated in FIGS. 4 and 5.

Figure 4:
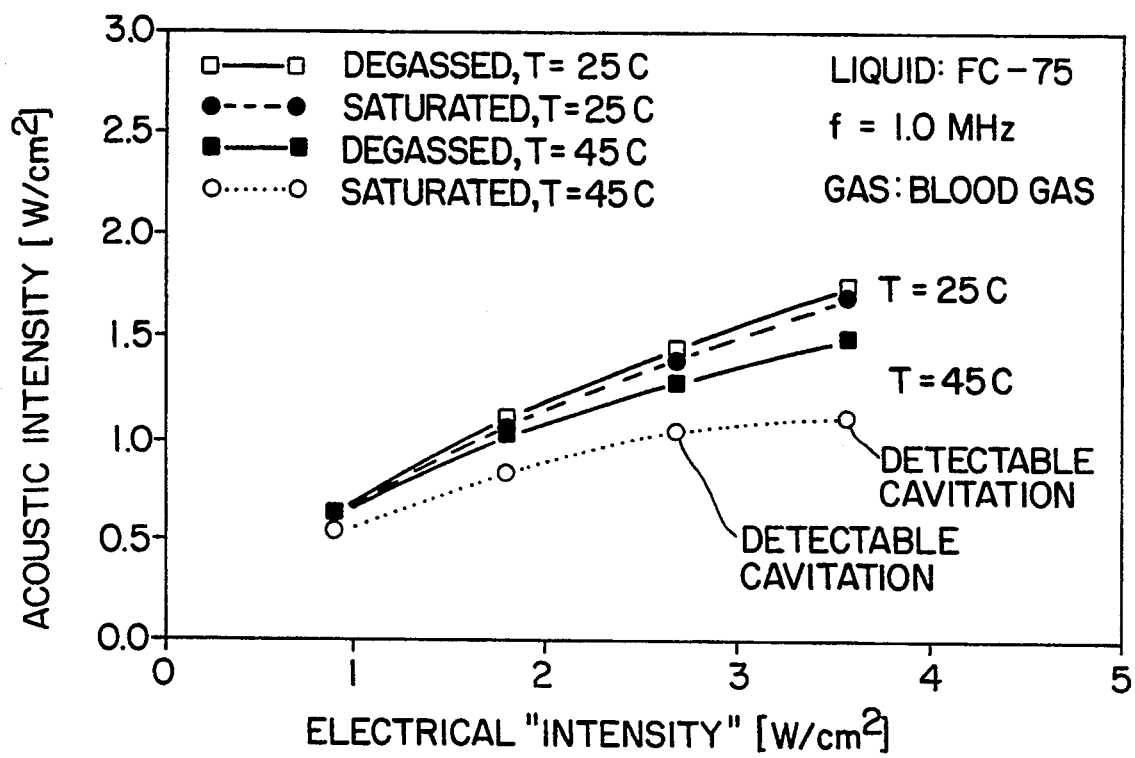
FIG. 4 is a graph plotting the attenuating effects of gas saturation on a PFC liquid.

As seen in FIG. 4, at 25° C. and at an electrical intensity of about 3 W/cm$^2$, cavitation was detected in the gassed PFC liquid. However, at the same temperature and electrical intensity, cavitation was not detected in the degassed PFC liquid. The cavitation in the gassed PFC liquid resulted in a marked dissipation of power.

Figure 5:
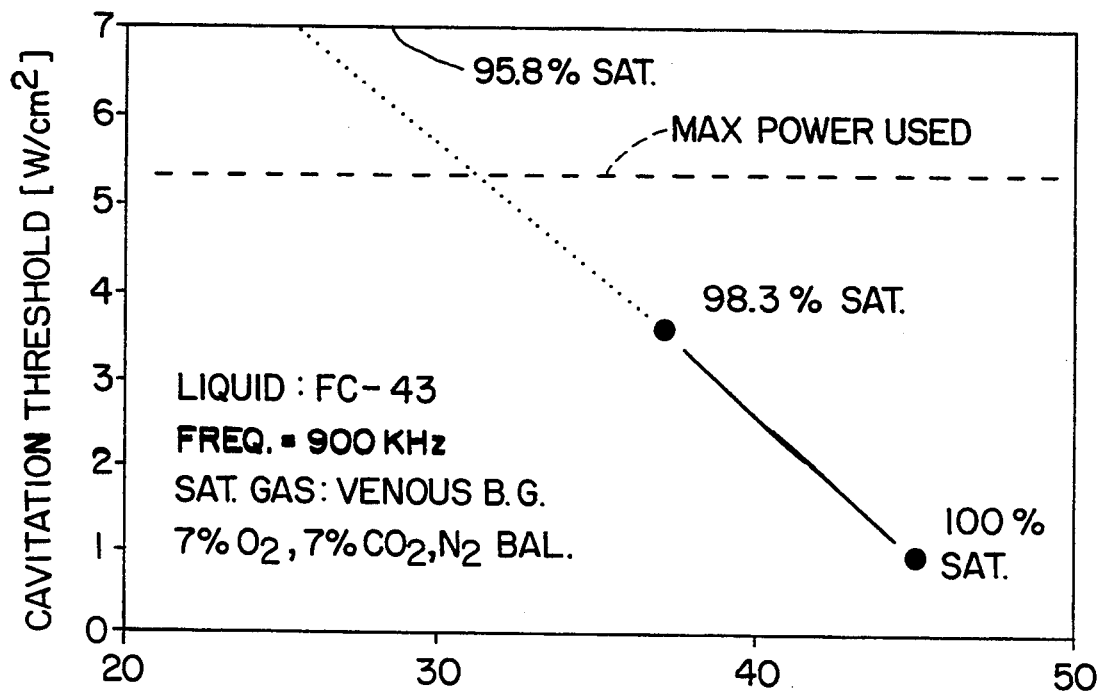
FIG. 5 is a graph plotting the cavitation threshold of a PFC liquid based upon the liquid's temperature and gas saturation level.

The data plotted in FIG. 5 demonstrates that the threshold for cavitation is dependent upon gas saturation and temperature. Specifically, FIG. 5 demonstrates that cavitation occurred more readily at higher percentages of gas saturation and temperature.

In vivo tests were performed on an anesthetized adult sheep which was intubated with a bifurcated bronchial catheter. There, a degassed PFC liquid was used to fill the cervical segment of the sheep's right apical lobe. Ultrasonic images were observed as the degassed PFC liquid filled the sheep's lung. While the lung was being filled, the sheep's lung region went from completely black to brightly lit.

Moreover, an image of a bag of a degassed PFC liquid suspended in an air-equilibrated water environment revealed a dark region while an image of the water environment revealed a white cloud. The cloudy image was associated to sound reflections from the air bubbles in the water. When the PFC liquid was not degassed, ultrasound imaging of the lung was unsuccessful.

It is evident from the foregoing that various modifications can be made to the embodiments of this invention without departing from the spirit and/or scope thereof which will be apparent to those skilled in the art. Having thus described the invention, it is claimed as follows:

That which is claimed is:

1. A process for removing gas emboli from a cavity, space, void or gap present in or around a patient's gastrointestinal tract, uterus, bladder, nasal cavity, sinus cavity or acoustic canal, said process comprising the steps of:

(a) degassing a perfluorocarbon liquid, (b) delivering the degassed perfluorocarbon liquid to a cavity, space, void or gap present in or around the patient's gastrointestinal tract, uterus, bladder, nasal cavity, sinus cavity or acoustic canal containing a gas emboli, (c) permitting the degassed perfluorocarbon liquid to absorb at least a portion of the gas emboli to form an emboli-containing perfluorocarbon liquid, and (d) removing from the cavity, space, void or gap present in or around the patient's gastrointestinal tract, uterus, bladder, nasal cavity, sinus cavity or acoustic canal the emboli-containing perfluorocarbon liquid.

2. A process as recited in claim 1, wherein a biological agent is mixed with the degassed perfluorocarbon liquid after step (a) but prior to step (b), and wherein at least some of the biological agent is permitted to be released from the perfluorocarbon liquid after step (b) but prior to step (d).

3. A process as recited in claim 1, wherein a biological agent is mixed with the perfluorocarbon liquid during step (a), and wherein at least some of the biological agent is permitted to be released from the perfluorocarbon liquid after step (b) but prior to step (d).

4. A process as recited in claim 1, wherein a biological agent is mixed with the perfluorocarbon liquid prior to step (a), and wherein at least some of the biological agent is permitted to be released from the perfluorocarbon liquid after step (b) but prior to step (d).

5. A process as recited in claim 1 wherein, prior to step (b), the perfluorocarbon liquid is heated to a temperature designed to hypothermically treat the patient.

6. A process as recited in claim 5, wherein a biological agent is mixed with the degassed perfluorocarbon liquid after step (a) but prior to step (b), and wherein at least some of the biological agent is permitted to be released from the perfluorocarbon liquid after step (b) but prior to step (d).

7. A process as recited in claim 5, wherein a biological agent is mixed with the perfluorocarbon liquid during step (a), and wherein at least some of the biological agent is permitted to be released from the perfluorocarbon liquid after step (b) but prior to step (d).

8. A process as recited in claim 5, wherein a biological agent is mixed with the perfluorocarbon liquid prior to step (a), and wherein at least some of the biological agent is permitted to be released from the perfluorocarbon liquid after step (b) but prior to step (d).

9. A process as recited in claim 1, wherein, prior to step (b), the perfluorocarbon liquid is heated to a temperature designed to hypothermically treat the patient.

10. A process as recited in claim 9, wherein a biological agent is mixed with the degassed perfluorocarbon liquid after step (a) but prior to step (b), and wherein at least some of the biological agent is permitted to be released from the perfluorocarbon liquid after step (b) but prior to step (d).

11. A process as recited in claim 9, wherein a biological agent is mixed with the perfluorocarbon liquid during step (a), and wherein at least some of the biological agent is permitted to be released from the perfluorocarbon liquid after step (b) but prior to step (d).

12. A process as recited in claim 9, wherein a biological agent is mixed with the perfluorocarbon liquid prior to step (a), and wherein at least some of the biological agent is permitted to be released from the perfluorocarbon liquid after step (b) but prior to step (d).

* * * * *